US008299930B2

(12) United States Patent
Schmid-Schonbein et al.

(10) Patent No.: US 8,299,930 B2
(45) Date of Patent: Oct. 30, 2012

(54) DEVICES, SYSTEMS AND METHODS TO CONTROL CALORIC INTAKE

(75) Inventors: Geert W. Schmid-Schonbein, Del Mar, CA (US); Angelina Altshuler, Danville, CA (US); Casey Gorish, San Diego, CA (US); Kunal Sukhija, Palos Verdes Estates, CA (US); Amanda Williams, San Diego, CA (US); Michael Wu, Sacramento, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 496 days.

(21) Appl. No.: 12/612,588

(22) Filed: Nov. 4, 2009

(65) Prior Publication Data

US 2010/0109876 A1   May 6, 2010

Related U.S. Application Data (60) Provisional application No. 61/111,335, filed on Nov. 4, 2008.

(51) Int. Cl.
*G08B 23/00* (2006.01)
(52) U.S. Cl. .................. 340/573.1; 340/3.1; 128/921
(58) Field of Classification Search .......... 340/573.1, 340/691.1, 691.6, 3.1, 3.31, 5.1, 5.2; 702/187, 702/189; 73/865.4; 434/127; 128/921
See application file for complete search history.

(56) References Cited

U.S. PATENT DOCUMENTS

| 5,908,301 | A  | * | 6/1999 | Lutz ........................... 434/236 |
| 6,558,165 | B1 | * | 5/2003 | Curry et al. ................. 434/236 |

OTHER PUBLICATIONS

British Medical Journal: Mandometer used in Swedish program helps obese children lose weight. News-Medical.net, Jan. 6, 2010, http://www.news-medical.net/news/20100106/British-Medical-Journal-Mandometer-used-in-Swedish-program-helps-obese-children-lose-weight.aspx.

* cited by examiner

*Primary Examiner* — Toan N Pham
(74) *Attorney, Agent, or Firm* — Moazzam & Associates, LLC (57) ABSTRACT

Devices, systems and methods are disclosed which relate to training a user in controlling and limiting total calorie consumption, and consequently body weight, by encouraging the user to perform specified consuming actions such as chewing slowly, adjusting a time interval between bites, detecting the early points of satiation, etc. The disclosure is therefore a "calorie pacer" that naturally reduces calorie consumption by re-teaching a user how to eat on a step-by-step basis. The slower eating pace results in a person feeling full before the intake of excessive food portions. The result is fewer calories consumed. Sensors and microcontrollers throughout a place setting are utilized to prompt the user, for example, when to take bites, how big of a bite to take, when to take a drink, etc and record the data in an efficient manner that allows for analysis, monitoring of progress, and personalized feedback.

22 Claims, 10 Drawing Sheets

DEVICES, SYSTEMS AND METHODS TO CONTROL CALORIC INTAKE

This application claims priority to U.S. Provisional Patent Application Ser. No. 61/111,335, filed Nov. 4, 2008, the content of which is hereby incorporated by reference herein in its entirety into this disclosure.

BACKGROUND OF THE INVENTION

1. Field of the Invention

The present invention relates to health and nutrition. In particular, the present invention relates to devices and methods for controlling caloric intake which results in weight gain or loss.

2. Background of the Invention

Uncontrolled eating habits and calorie overconsumption have resulted in rising obesity rates. Obesity may be defined as a medical condition in which excess body fat has accumulated to the extent that it may have an adverse effect on a person's health, leading to reduced life expectancy and/or increased health problems. The health and social impacts of obesity are numerous. Obesity increases the risk of illness from more than 30 serious medical conditions including hypertension, diabetes, and coronary heart disease, turning out to be one of the top killers in the country. Those that suffer from extreme obesity, that is, having a Body Mass Index (BMI) of greater than 30, experience mobility issues and in some cases must resort to expensive personal transportation devices. This is steadily increasing the cost of healthcare in the country, in addition to the constant social stigmatization and discrimination in employment and academic settings.

The condition has swept the nation—currently 127 million adults (over half of the population) in the U.S. are overweight, 60 million are obese, and 9 million are severely obese. The obesity epidemic is predicted to get worse. Many experts suggest that if nothing is done to curb this problem, well over 80% of our nation will be overweight by 2010. There have been several efforts to curb the obesity epidemic, but most are misguided or ineffective when applied. Diet programs designed to reduce overweight or prevent weight gain lack a long-term perspective and the ability to curtail calorie overconsumption in the long run for months, years, or decades. Expensive diet programs, specialty health foods, and even diet pills do not stand a chance against cheap, widely available, and massively advertised food. A lack of proper guidance ultimately results in the uncontrolled eating habits leading to obesity. Exercise regimens may be ineffective as weight control measures when accompanied by calorie overconsumption at a level that is in excess of what is needed to maintain daily caloric needs. In many instances, weight control can only be brought about by calorie intake control. This can be by bariatric surgery, i.e. forcibly, or voluntarily food intake reduction. Surprisingly, there are few other options, since digestive enzyme inhibitors have given mixed results.

What is needed is a treatment to control calorie intake and weight gain over long periods of time within a traditional dietary selection specific for individual families and communities. The treatment has to address calorie consumption at a very basic level by changing a person's eating habits. The treatment should be simple to administer, effective and capable of aiding individuals adjust their consumption of calories over a life-time. It should be a change in eating style that leads to a lifelong adjustment to reduced and decelerated calorie consumption, not a short term or transient change with high probability for recurrence of older eating habits that are associated with calorie overconsumption and weight gain. The treatment should provide a gradual and permanent transition in eating habits that lead from high calorie consumption to ever reducing calorie intakes until ideal bodyweights are approached.

The first key issue in calorie consumption is the "rate of calorie consumption" during individual meals. During the time period between the beginning of a meal and the feeling of satiation (about 15 min in an average adult) the rate of calorie consumption needs to be minimized and used to consume calories at a deliberately reduced rate in order to minimize calorie intake before the end of a meal. Such a habit of slow eating needs to be trained over long periods of time (months, years) in order to become permanently accepted even in the presence of challenges to the contrary. Chewing periods need to be maximized and easy calorie consumption (e.g. liquid calorie consumption) minimized. All of these habits require a systematic training to eat deliberately slow in an environment (e.g. in terms of culinary traditions, economics, etc.) that is compatible over long periods, i.e. a lifetime. Learning to eat slowly can be achieved within family traditions ("Grandma's cooking is the best anyhow") without the need for specific and often costly diet programs that offer no long term perspective ("can't wait to get off this diet").

A second critical issue is to avoid calorie consumption after the feeling of satiation has been detected (i.e. stuffing). The instant satiation sets, calorie consumption has to be terminated, irrespective of the amount of food still available. Instructions needs to be given to stop eating and leftovers stored until the next meal. Discontinuation of calorie consumption past the point of satiation should be rewarded. Slow eating and cessation of calorie consumption at a meal need to be trained for long periods of time by means of a new technology in form of "smart place sets" that help monitor calorie consumption and provide feedback and guidance for slow eating and limited calorie consumption.

SUMMARY OF THE INVENTION

The present invention provides systems, devices, and methods designed to control the rate as well as total calorie consumption at a meal, and consequently body weight of a user, by encouraging the user to perform specified consuming actions such as chewing slowly and for progressively longer periods of time, adjusting a time interval between bites, placing a utensil down between bites, terminating eating at the point of satiation, etc. The invention is therefore a "calorie pacer" that naturally reduces calorie consumption by re-teaching a user how to eat on a step-by-step basis. The slower eating pace results in a person feeling full at a point when a minimal number of calories has been consumed (and stuffing has been avoided). Current research journal articles demonstrate health benefits from consuming fewer calories including a reduced risk of cancer, heart disease, diabetes, hypertension, among many potential conditions. The present invention helps a user minimize the rate of calorie and total calorie consumption during a meal by dynamically presenting the user with suggestions for low calorie fluid consumption, pacing the meal, maximizing chewing action, and ceasing consumption when there is no more hunger sensation. The present invention therefore assists in the retraining of eating habits towards a lifetime of controlled calorie consumption. Patterns in the user's consumption are associated with desired patterns in order to regulate the consumption of the user. Over time, the user's consumption patterns or eating habits are altered, resulting in a desired outcome such as weight loss.

In one exemplary embodiment, the present invention is a system for controlling caloric intake of a user. The system includes at least one microcontroller including a processor and a memory (either connected or wireless), an input in communication with the microcontroller, an output in communication with the microcontroller, a sensor in communication with the microcontroller, scales under plates and glasses to detect weight change, and a logic unit on the memory. The logic includes detecting a first consuming action performed by the user, and prompting the user to perform a second consuming action after a time interval until the user signals they are no longer hungry.

In another exemplary embodiment, the present invention is a device for controlling the rate and the total amount of caloric intake of a user. The device includes a processor, a memory in communication with the processor, an input in communication with the processor, an output in communication with the processor, a sensor in communication with the processor, and a logic unit on the memory. The logic includes detecting a first consuming action performed by the user, and prompting the user to perform a second consuming action after a time interval.

In yet another embodiment, the present invention is a method for monitoring and regulating a caloric intake of a user. The method includes detecting a first consuming action performed by the user during a consumption of a meal, and prompting the user to perform a second consuming action after a time interval. The first consuming action is detected by a sensor and the second consuming action is prompted by an output. Scales are built into a placemat holding the plate and a coaster holding the glass. As food and drink is consumed, changes in weight are sensed and display to the user via a microprocessor that records the sequence of events during the meal. This could be combined with the simple sensor idea. The scale sensors provide input for type of food or drinks such that from the weight change an approximate amount of calories are computed, for instance using calorie standard tables, and communicated.

DETAILED DESCRIPTION OF THE INVENTION

The present invention controls overall calorie consumption by monitoring a user's eating patterns and by directing the user how to appropriately consume a meal. Logic on a computer readable medium is paired with a processor and at least one sensor to determine various patterns in consuming actions performed by a user during consumption of a meal. The sensors detect a consuming action, such as by the motion of a utensil held by the user. Based on patterns determined in the user's consuming actions, the logic may determine that adjustments to the user's consumption are needed. These adjustments are communicated to the user in the form of suggestions conveyed via an output. For instance, a display outputs a message to remind the user to slow down the frequency of consuming actions, wherein the frequency is measured by detecting a utensil being picked up and set down. Users can be trained via a video, comprehensive instruction booklets, classes, etc. An initial trial or learning period may be undertaken to train both the system and the user. Furthermore, a user profile may be stored on a memory within the system, the user profile including the user's consumption patterns, physical statistics of the user, as well as programmed goals and desired patterns for the user. These elements may be separate components of a system, or combined with the utensil resulting in a highly compact intelligent calorie-pacing utensil.

Various configurations of the present invention are described in the embodiments presented below. However, for clarity: "Logic", as used herein and throughout this disclosure, refers to any information having the form of instruction signals and/or data that may be applied to affect the operation of a processor. Examples of "processors" are computer processors (processing units), microprocessors, digital signal processors, controllers and microcontrollers, etc. Logic may be formed from signals stored in a memory coupled to a processor. A software program is one example of such logic. Examples of memories that may store logic include RAM (random access memory), flash memories, ROMS (read-only memories), EPROMS (erasable programmable read-only memories), and EEPROMS (electrically erasable programmable read-only memories). Logic may also be comprised by digital and/or analog hardware circuits, for example, hardware circuits comprising logical AND, OR, XOR, NAND, NOR, and other logical operations. Logic may be formed from combinations of software and hardware.

A "utensil", as used herein and throughout this disclosure, refers to any tool used to insert food into the mouth. Examples of a utensil include a spoon, a fork, a knife, a cup, chopsticks, etc.

A "consuming action", as used herein and throughout this disclosure, refers to the consumption of any specific measure of a portion of food suitable for one bite. The specific measure may be a tablespoonful, forkful, mouthful, or a specific weight measured by a weight sensor embedded in the tableware or the utensil. A bite is an example of one consuming action.

For the following description, it can be assumed that most correspondingly labeled structures across the figures (e.g., 132 and 232, etc.) possess the same characteristics and are subject to the same structure and function. If there is a difference between correspondingly labeled elements that is not pointed out, and this difference results in a non-corresponding structure or function of an element for a particular embodiment, then that conflicting description given for that particular embodiment shall govern.

Figure 1A:
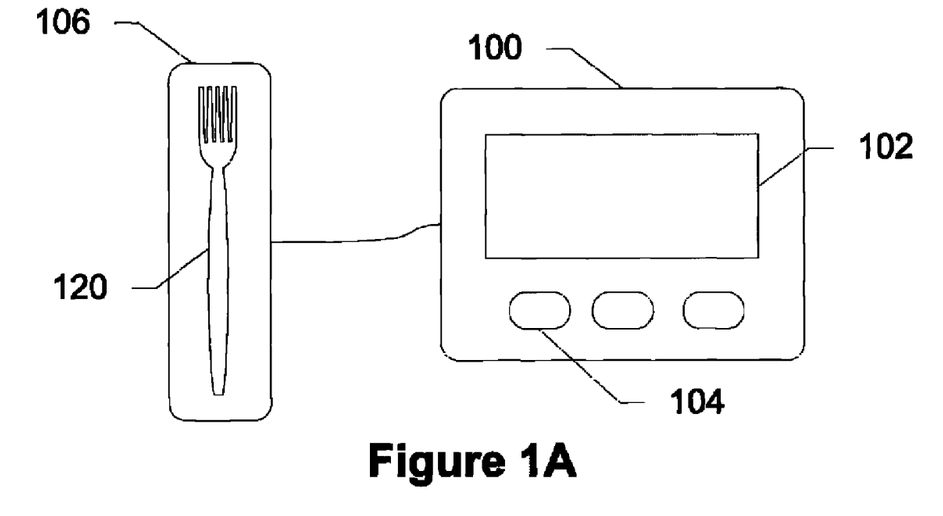
FIGS. 1A-1B show a system for controlling weight gain, according to an exemplary embodiment of the present invention.
Figure 1B:
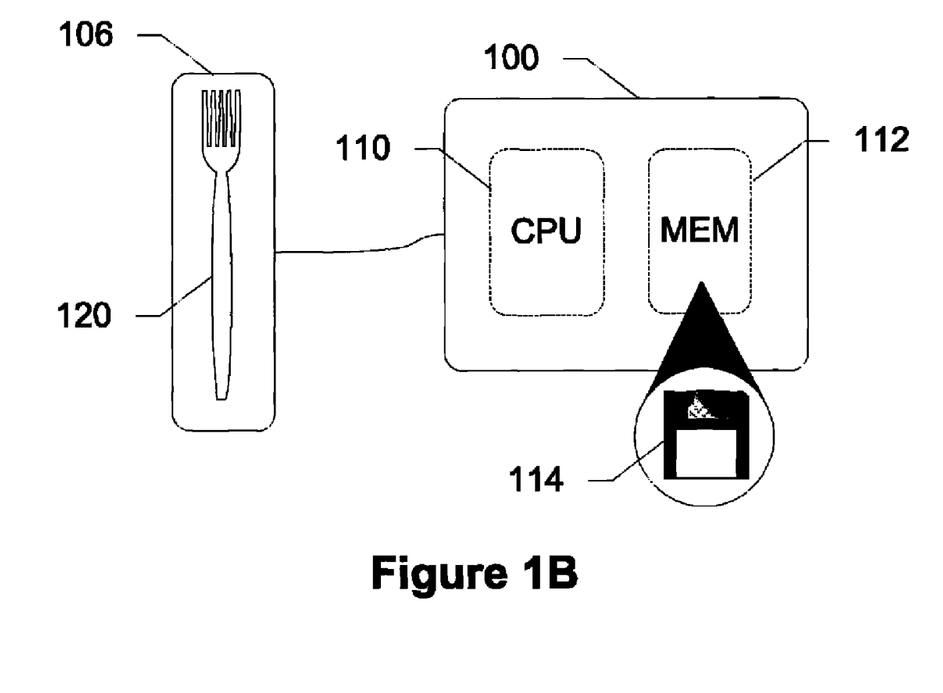

FIGS. 1A and 1B show a system for controlling overall calorie consumption, according to an exemplary embodiment of the present invention. The system includes a microcontroller portion 100 having a display 102 and buttons 104, as shown in FIG. 1A. The microcontroller portion is in communication with a sensor 106 via a wired or wireless connection. Sensor 106 detects the presence of a utensil, for instance, fork 120, and transmits a signal to microcontroller 100 via a wired or wireless connection. Microcontroller 100 further includes a CPU 110 and a memory 112, as shown in FIG. 1B. Memory 112 stores logic 114.

Before beginning consumption of a meal, a user of the system activates the system by, for instance, pushing one of buttons 104. Buttons 104 are the input in the present embodiment. However, other inputs will be apparent to one having ordinary skill in the art, such as microphones, touchscreens, etc. The user may also activate the system by raising fork 120 off of sensor 106. Sensor 106 generates a presence signal that is processed by CPU 110. Upon commencement of a meal, logic 114 is programmed to suggest to the user, via display 102, a consuming action, or a suggestion to adjust the user's consumption of the meal. For instance, the logic may convey a message to the user to consume a bite or portion of the meal. The message may read: "Please take a bite of the meal" or "Are you still hungry?" as a message on display 102. Although display 102 is shown as an exemplary output, other outputs will be apparent, such as a speaker narrating a voice instruction, a buzzer, LED lights, a vibrator, etc.

When the user follows the suggestion by taking a bite, sensor 106 determines that fork 120 is being used, and appropriately sends a signal to microcontroller 100. Sensor 106 may be any sensor capable of detecting a presence or motion of utensil 120, such as a weight sensor, light sensor, capacitance sensor, accelerometer, etc. So long as a sensor 106 can determine the presence or movement of utensil 120, the measured signal can be used by logic 114 to determine a plurality of consuming actions by the user. When the user places fork 120 upon sensor 106 between bites, microcontroller 100 measures the time until fork 120 is picked up again. The acquired data is used to determine a time interval between subsequent bites, a time for chewing, and an estimated rate of calorie consumption. Other measurements include fat calories consumed, protein consumed, percentage of daily values consumed, etc., based upon a meal profile that is activated by the user before beginning consumption of the meal. These measurements are recorded in a user profile stored within memory 112, and can be compiled into a consumption pattern for the user. These measurements may further include a time, day, etc. such that this information is available and/or can be used for determining timing intervals of bites. Furthermore, the measurements can be compared with a set of target or desired consumption patterns. An example of a consumption pattern is described in FIG. 4.

Further embodiments include sensors to determine plate and glass weight in communication with the microcontroller. The display screen serves to display on-line weight/computed calorie intake during a meal, instructions for pacing during the meal, feedback regarding the state of satiation, meal termination, etc. The display is a touchscreen in some embodiments allowing it to function as an input as well.

Based on any combination of detected/recorded consuming actions pattern or a pre-defined consumption pattern, the system presents suggestions to the user to modify his or her consuming actions to conform to a desired pattern. The modifications may be minimal at first, such as gently encouraging the user to chew slowly, to take more time between bites or portions, to drink water, or to adjust the size of a portion or bite of the meal. The system may further suggest general eating habits for the user, such as chewing the food to the point of no texture, or ceasing eating when the user is no longer hungry. Other helpful suggestions include fully swallowing a bite before taking the subsequent bite, taking breaks, etc.

Figure 2:
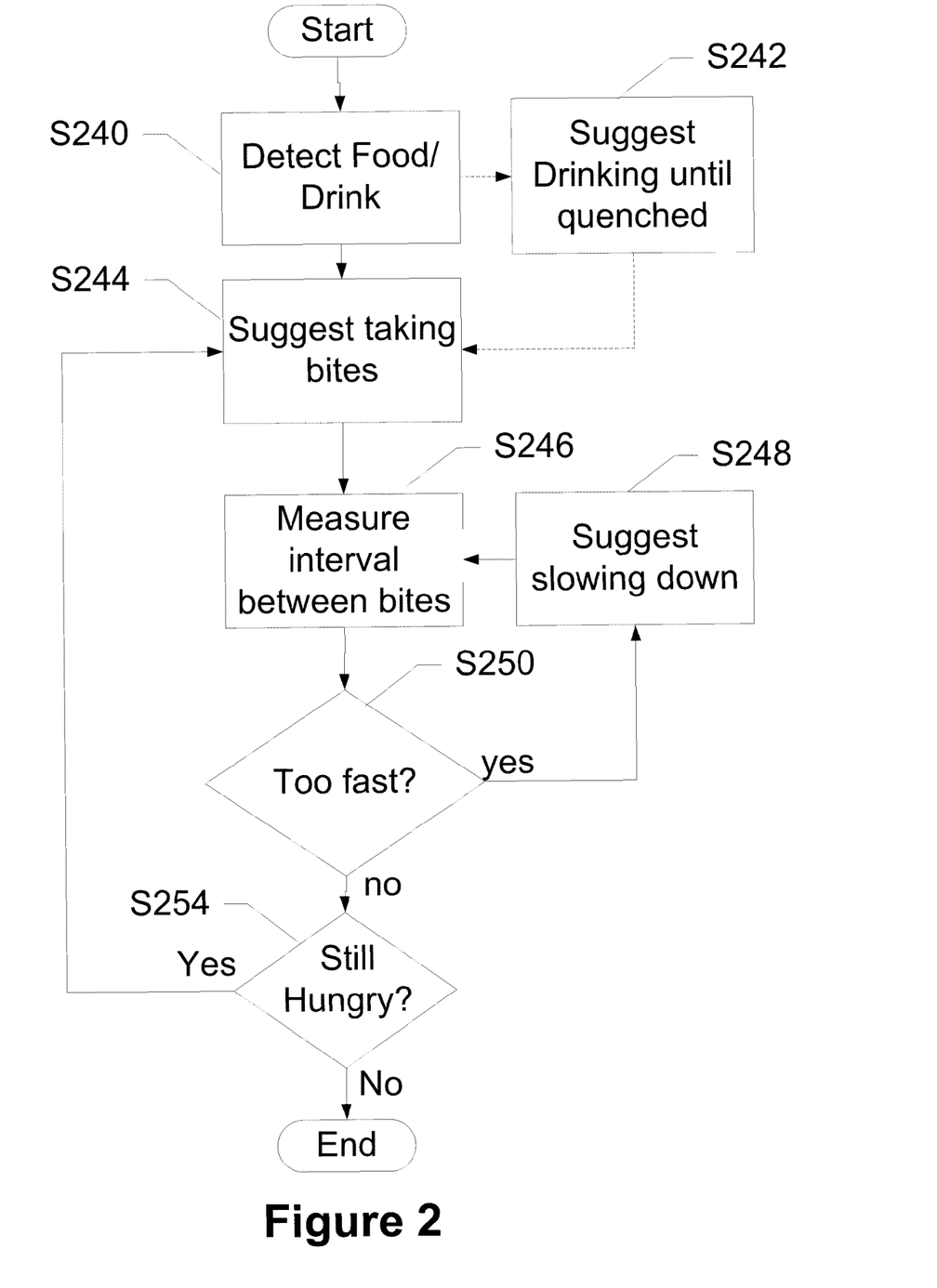
FIG. 2 shows a method for controlling weight gain, according to an exemplary embodiment of the present invention.

As described above, the present invention is predicated upon the fact that increasing a user's awareness about the rate of his or her calorie consumption and simultaneously encouraging the user to adjust this rate will result in more effective control of calorie consumption, and therefore, weight. A method for effectively controlling the rate of calorie consumption is described with respect to the exemplary embodiment of FIG. 2. A method of controlling caloric intake begins with the detection of the presence of food or drink S240. This detection occurs through sensors within the system, incorporated within tableware, or alternatively, through a command submitted by the user. Optional step S242 suggests that the user drinks water before starting. This helps to lower the user's appetite for food. A suggestion is then indicated that the user take a bite S244. The system measures the time interval between bites S246. This may be accomplished for instance via a sensor measurement that detects when a utensil is laid down. Alternatively, this may be measured by a weight of a portion of food consumed or by sensing a subject exhibiting chewing behavior. Other means of determining a bite action will be apparent in light of the various sensors described above. Upon determining a bite interval, the bite interval is compared with a predefined or desired bite interval associated with the user and derived from control measurements. The bite interval may be recorded and stored in a user profile. With this information, the system determines whether or not the user is taking bites too fast S250. If it is determined that the user is taking bites too fast, then a suggestion is made to the user to slow down S248. This slowing can be accomplished by, for example, increasing the time between bites, chewing slower, chewing longer, etc. The system continues to measure the interval between bites S246 and continues encouraging the user to adjust their consuming actions until a desired pattern is reached. The system then queries the user whether the user is still hungry S254. The prompt or suggestion may be presented periodically, after a predefined number of bites is reached, or after a specified caloric intake is attained. The predefined and specified data may be stored in a profile associated with the user. Until the user responds to prompt S254 in the negative, the system continues to provide suggestions S244 to the user. Then, the recorded pattern may be stored for further retrieval, and the method ends.

Figure 3:
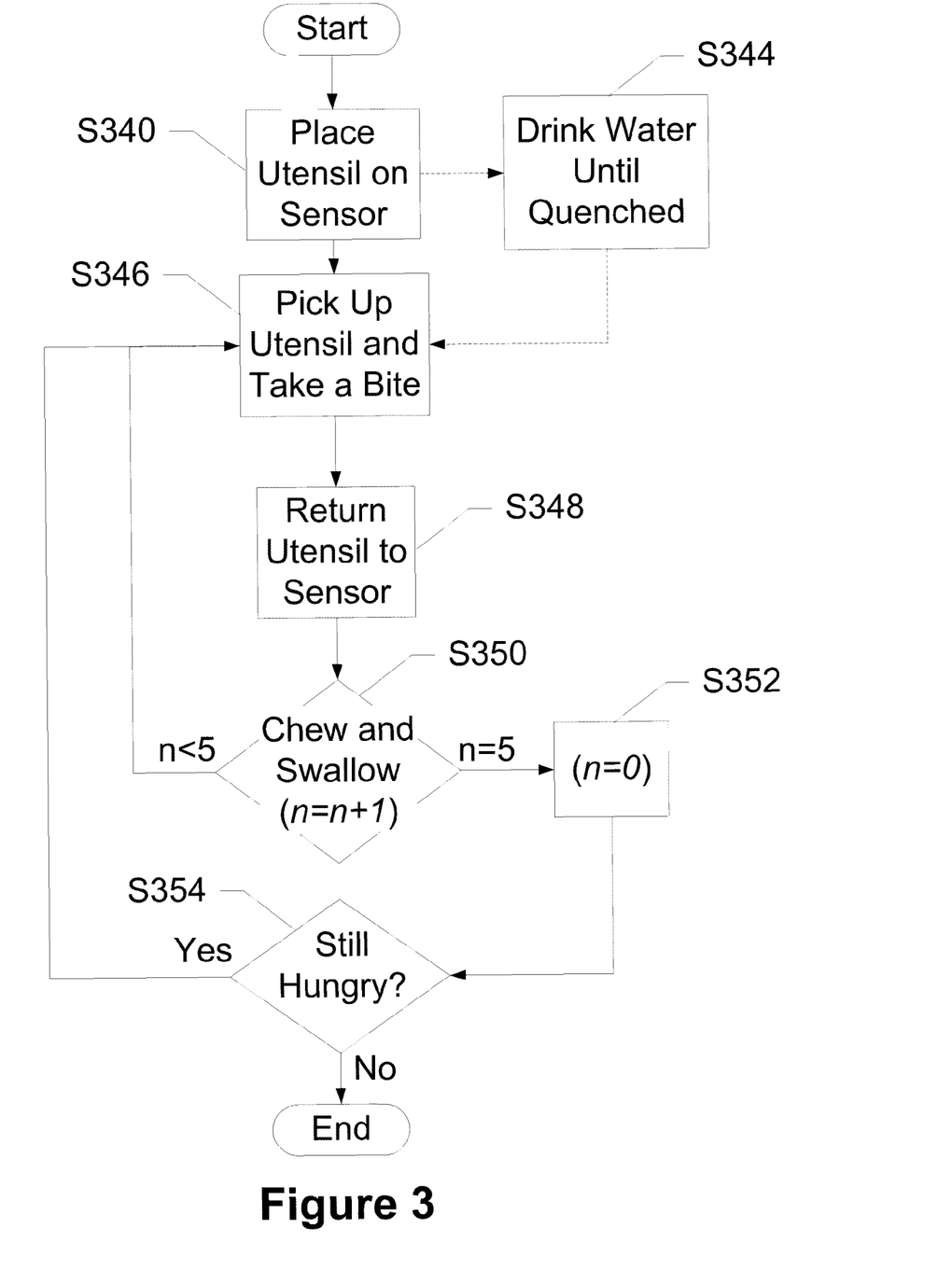
FIG. 3 shows another method of controlling caloric intake, according to an exemplary embodiment of the present invention.

FIG. 3 shows another method of controlling caloric intake, according to an exemplary embodiment of the present invention. In this embodiment, the method begins with a user placing an eating utensil on a sensor S340. A drink of water is suggested S344. A suggestion is made to pick up the utensil and take a bite of food S346. After taking a bite, the user returns the utensil to the sensor S348. This indicates to the system that a bite has been taken, and a counter is incrementally increased S350. After every 5 bites a prompt is provided to the user to check if their hunger is satisfied S354. The user may indicate that he wishes to continue eating, at which point the system continues suggesting consuming actions S346. If the user enters that he or she is no longer hungry, then a message may be sent to stop eating, the remaining food may be stored for later consumption, and the method ends. The user is rewarded and encouraged by an oral/visual signal for compliance with the instructions. Thus, a user is regularly reminded to stop eating based on the number of bites taken, or the number of calories consumed.

As mentioned herein, exemplary embodiments of the present invention allow for recording of initial consumption patterns during a trial period, and store the patterns in a profile associated with the user. Subsequently, each time the user consumes a meal, the time intervals between bites are gradually increased. In further embodiments, the progress is logged and exported to a computer for further data processing.

Figure 4:
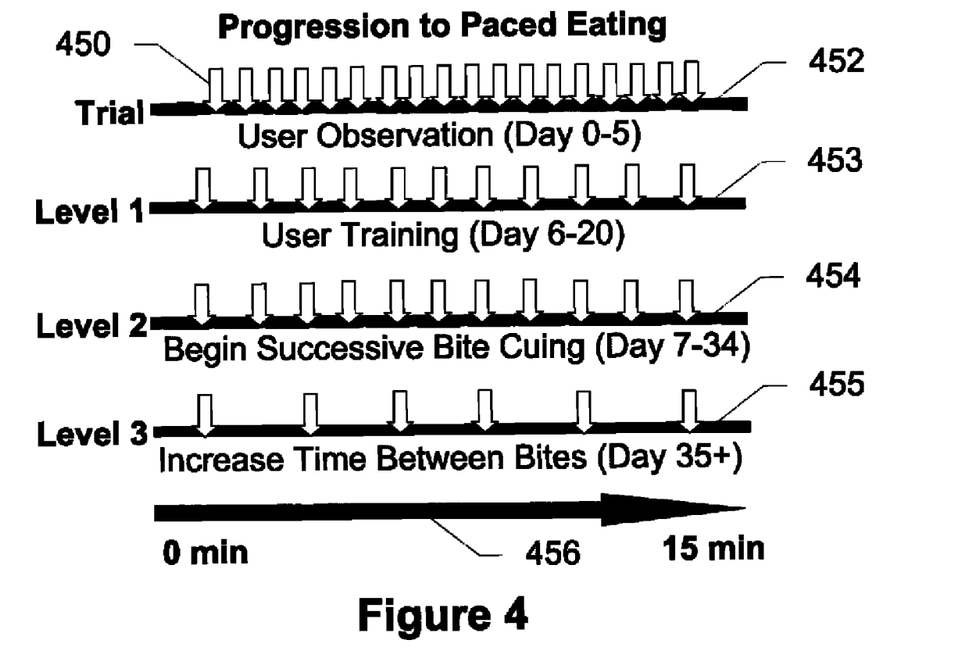
FIG. 4 shows a progression of paced eating, according to an exemplary embodiment of the present invention.

FIG. 4 shows a progression of paced eating, according to an exemplary embodiment of the present invention. In this embodiment, the chart includes arrows 450 indicating bites or portions of a meal arranged over a horizontal time axis 456. A sequence of bites 450 constitutes a trend or progression of a meal over time. The figure shows a trial level progression 452, a Level 1 progression 453, a Level 2 progression 454, and a Level 3 progression 455. The various levels are preprogrammed and stored as desired progressions. Alternatively, the progression is set at the time of each meal based on a previous consumption of a meal. For instance, during trial level progression 452, the system for controlling caloric intake observes the user's eating habits. As the user places a utensil down, the system determines that the user is between bites and can thus calculate a number of bites, a frequency of bites, calories consumed, etc. Trial level progression 452 is observed with bites 450 distributed along time axis 456. In embodiments of the invention, trial level progression 452 lasts for a few days or longer. During Level 1 progression 453, the user is trained to take a bite when prompted, to properly place their utensil after each successive bite, and to chew food properly. The user is also trained to drink and to stop eating when feeling full. In embodiments of the invention, Level 1 progression 453 lasts from day six until day twenty. After Level 1 progression 453 the user begins Level 2 progression 454. Level 2 progression 454 cues successive bites 450 by the user, indicated to the user via a display device, beep, vibration, etc. In embodiments of the invention, Level 2 progression 454 lasts between days seven and thirty-four. With Level 2 progression 454 finished, Level 3 progression 455 begins increasing the time between the user's bites 450. The user is prompted to take bites 450 less frequently, allowing the user more time between bites 450 to feel satiated. The user also properly digests food as the user has more time for chewing, resulting in optimal nutrient absorption.

Figure 5:
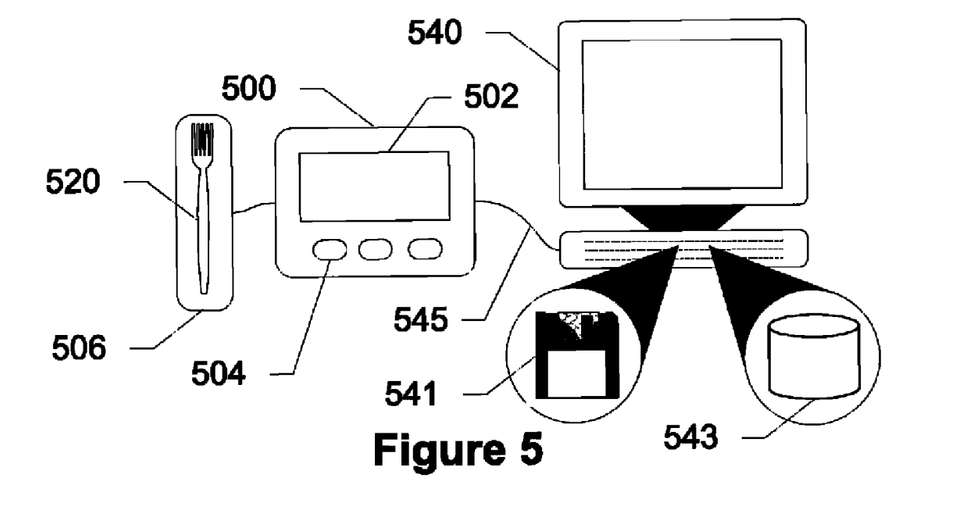
FIG. 5 shows an alternate system for controlling weight gain, according to an exemplary embodiment of the present invention.

As mentioned herein, the present invention may be incorporated in a system, with the various steps of the method being implemented in different system components. FIG. 5 shows an alternate system for controlling caloric intake, according to an exemplary embodiment of the present invention. The system of FIG. 5 includes an interface portion 500 having a display 502 and an input 504. However, in this system, the interface portion communicates input and output commands between a user and an external terminal 540. External terminal 540 houses the logic 542 and a database 543, the database including a user profile and/or a meal profile. External terminal 540 acts as the microcontroller of foregoing exemplary embodiments. The system also includes a sensor 506 to detect the presence/absence of a utensil such as fork 520 and transmits a signal that is received by logic 542 either via interface 544 or via a direct connection. Communication between interface 544, sensor 506, and terminal 540 may occur wirelessly or via interface cables.

According to the embodiment of FIG. 5, a user of the system activates the system by, for instance, pushing one of buttons 504 or by lifting fork 520 from sensor 506. Logic 542 suggests to the user, via display 502, a consuming action, or a suggestion to adjust the user's consumption of the meal. When sensor 506 determines that fork 520 is being used, a signal is transmitted to logic 542, and stored as a progression in database 543 to be compiled into a consumption pattern for the user, as described above.

In some embodiments the external terminal connects to a database of nutritional information. The connection can be through any data connection such as through a service provider or the INTERNET. The database of nutritional information includes caloric information such as calorie standard tables. A user may use these values instead of inputting the caloric information manually.

Figures 6A, 6B:
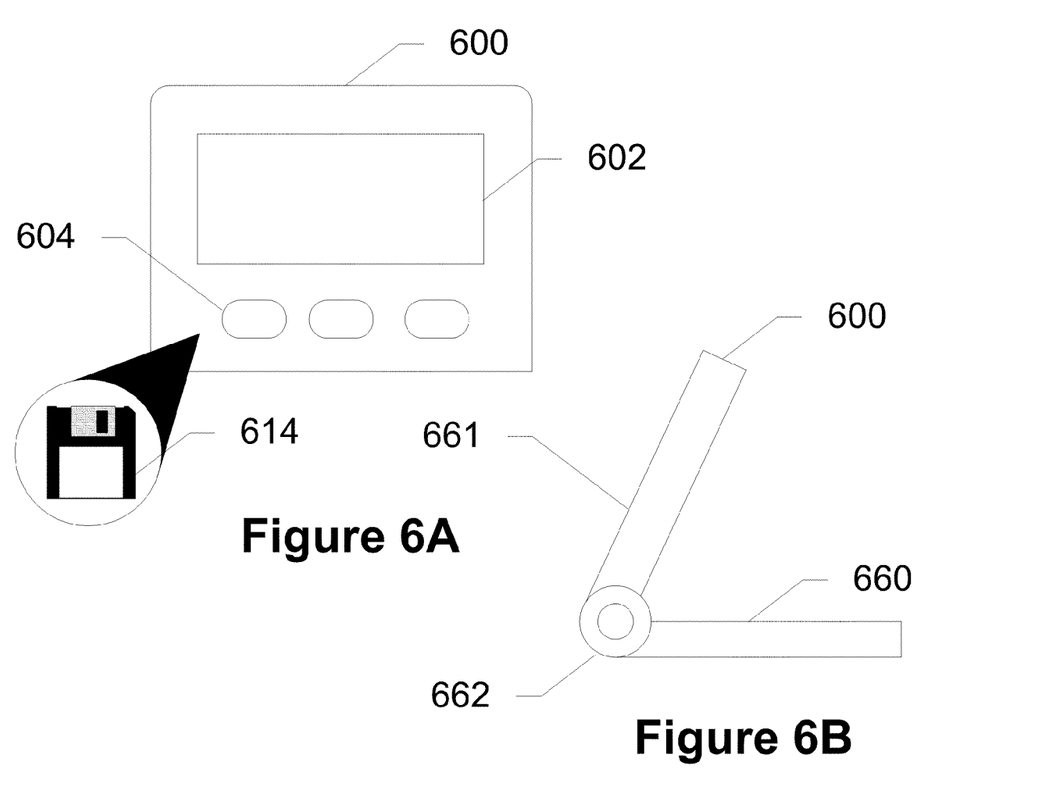
FIGS. 6A-6C show a sensor incorporated within a microcontroller, according to an exemplary embodiment of the present invention.
Figure 6C:
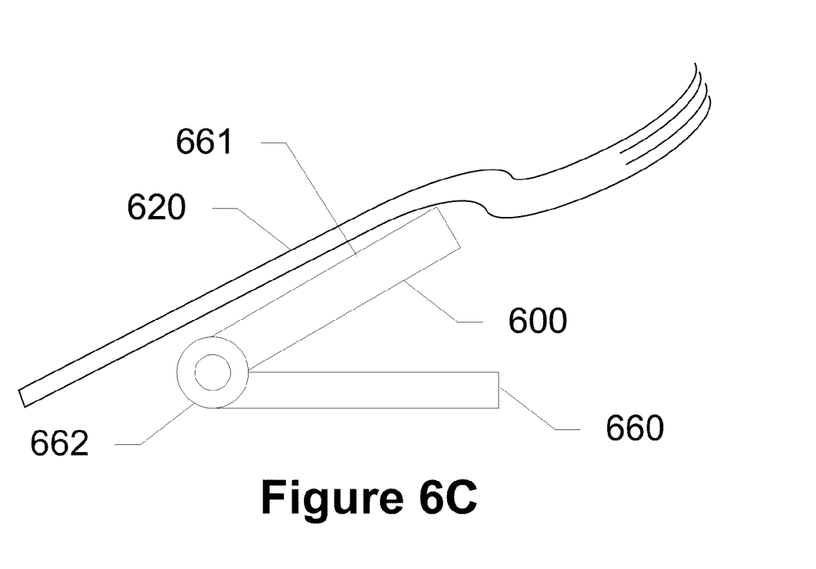

Other configurations of the system are possible. FIGS. 6A-6C show a microcontroller 600, which further incorporates a sensor within it. FIG. 6A shows the top view of microcontroller 600, including a display 602, input 604, and logic 614. From the side view of FIG. 6B, it can be seen that display 602 and input 604 are incorporated within a top portion 661, which is coupled via hinge 662 to a bottom portion 660. Hinge 662 is spring-loaded, such that if any additional weight, such as that of utensil 620, is added to the top portion 661, then the device 600 folds, activating a switch or sensor that generates a signal to be processed by logic 614. Hinge 662 may be outfitted with a spring such that microcontroller collapses under the weight of a utensil. Alternatively, top portion 661 may include sensors to detect the presence of utensil 620, such as those seen in the external sensor of FIG. 1. Microcontroller 600 may further include a transceiver for communication with an external terminal, or other external sensors such as the ones described in FIG. 8

Further embodiments include sensors to determine plate and glass weight in communication with the microcontroller. The display screen serves to display on-line weight/computed calorie intake during a meal, instructions for pacing during the meal, feedback regarding the state of satiation, meal termination, etc.

Figures 7A, 7B:
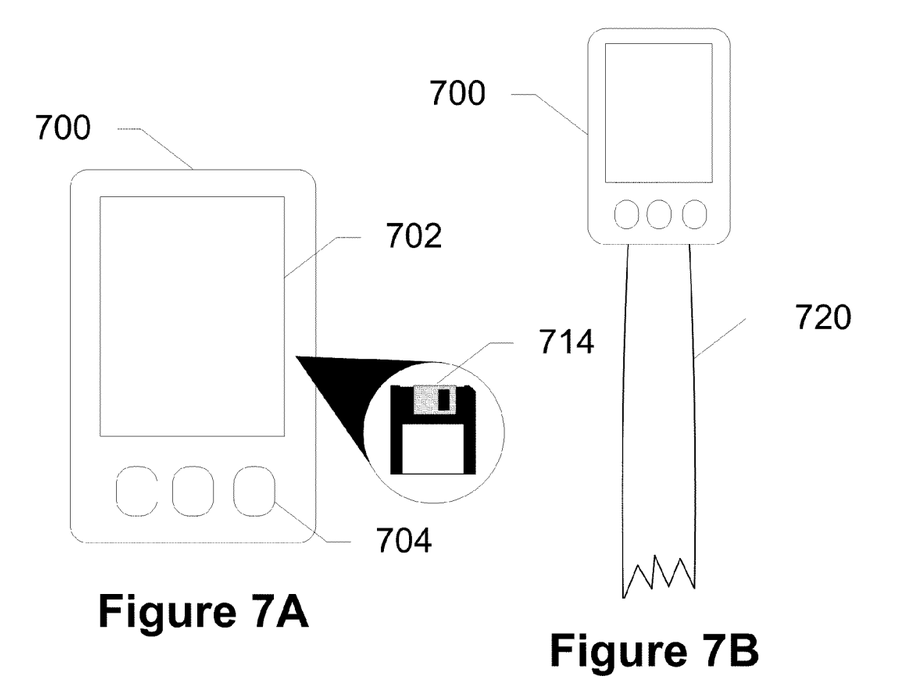
FIGS. 7A-7B show a portable device which is incorporated with a utensil, according to an exemplary embodiment of the present invention.

In some embodiments, the present invention is incorporated within a small and portable device which attaches to the end of utensil. The device instructs the user how to pace their caloric intake through the meal. An example of such a device is shown in FIGS. 7A-7B. Microcontroller 700 includes a display 702, an input 704, and a logic 714. The microcontroller 700 is small enough to be attached to the end of a utensil 720. Furthermore, a sensor can be incorporated into microcontroller 700 to detect a consuming action by the user. Such a sensor may be a light, capacitance, heat, pressure, or motion sensor such as an accelerometer. Microcontroller 700 is unclipped from utensil 720 for when utensil 720 is washed. Alternately, microcontroller 700 may be waterproof sealed for easy washing of utensil 720. Microcontroller 700 is small and positioned off of the eating surface so as not to bother or distract others at the table.

The microcontroller of FIGS. 7A and 7B includes a vibrator in alternate embodiments. The device still instructs the user to when to perform the next consuming action. However, if the user attempts to perform a consuming action before the next time interval has begun, then the vibrator activates, alerting the user that it is too soon to take the next bite.

Figure 8:
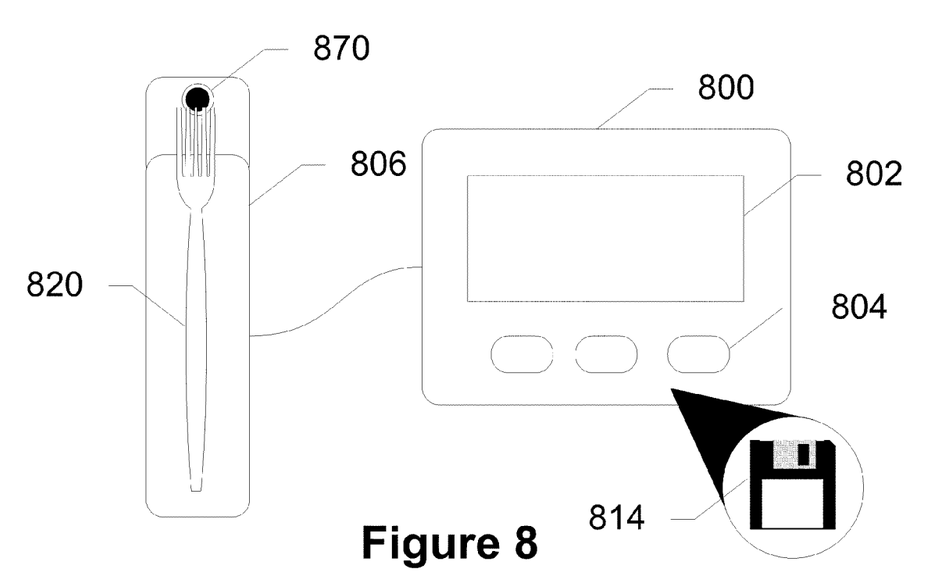
FIG. 8 shows another exemplary system embodying the present invention.

FIG. 8 shows another exemplary system embodying the present invention. Microcontroller portion 800 includes a screen 802, an input 804, and a logic 814. Microcontroller 800 communicates with a light sensor 806 having a light source 870 that detects the presence of a utensil such as fork 820. Signals generated by light sensor 806 constitute one of several actions undertaken by a user of utensil 820, such as taking a bite. Display 802 is used to suggest, for instance, that the user drink water, take the first bite of food, and place utensil 820 onto sensor 806. Logic 814 uses signals generated by sensor 806 to determine a bite interval, a chewing time, etc. As the user continues consuming the meal, display 802 displays constant reminders of the stages of eating (chewing, drinking, utensil setting down). Every few bites, display 802 asks the user the question "are you still hungry?" If the user answers this question "no" then the device recommends that the user stop consuming food. Microcontroller 800, through display 802, recommends that the remaining food be stored/refrigerated until the next meal or discarded and provides positive feedback for compliance. Display 802 shows messages such as, "Congratulations! You avoided unnecessary food intake and possible weight gain".

Figure 9A:
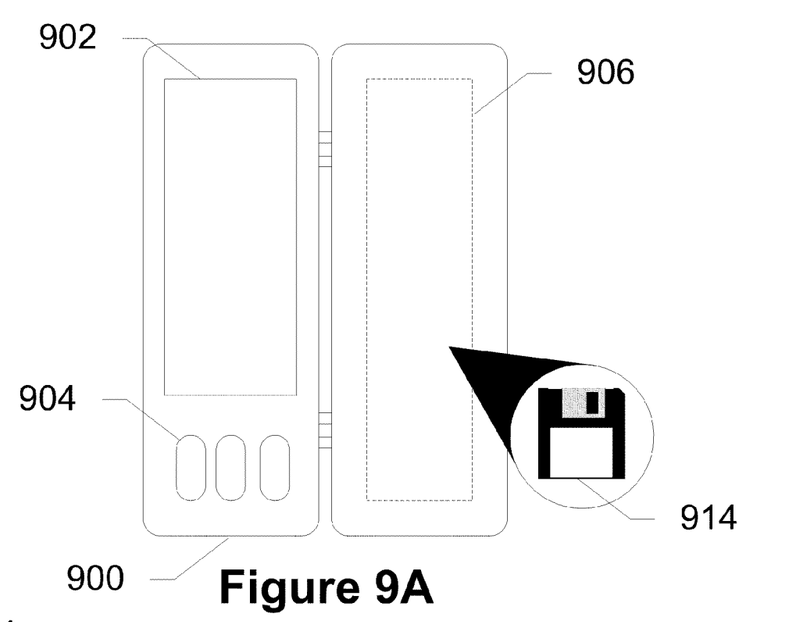
FIGS. 9A-9C disclose a device 900 that can be removably coupled to a utensil, according to an exemplary embodiment of the present invention.
Figures 9B, 9C:
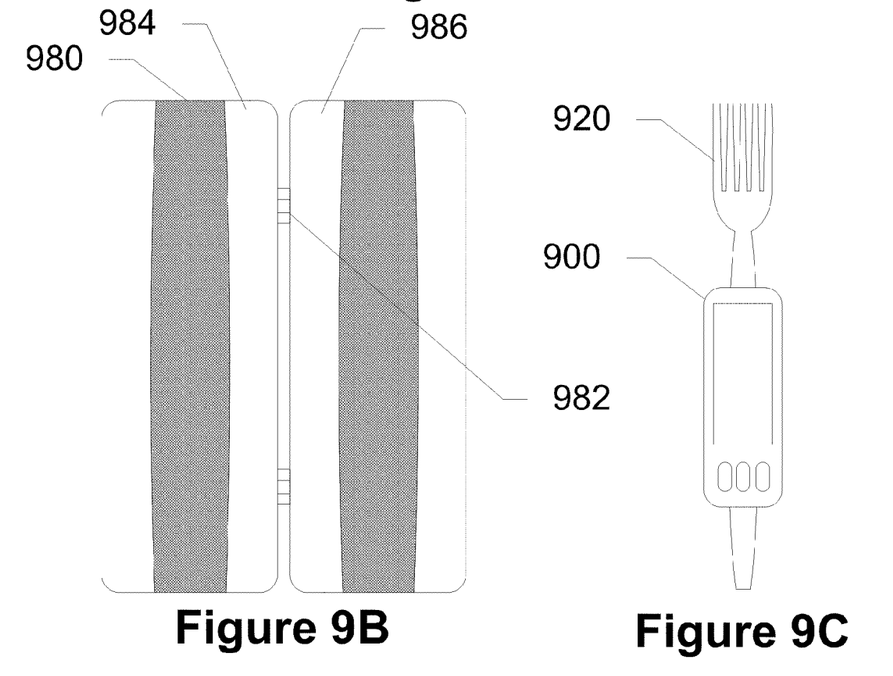

FIGS. 9A, 9B, and 9C disclose a microcontroller device 900 that can be removably coupled to a utensil 920, according to an exemplary embodiment of the present invention. In this embodiment, microcontroller 900 includes a display 902, a button 904, a sensor 906, a logic 914, a hinge 982, and a utensil channel 980. A user slips a utensil 920 into utensil channel 980 on either a front portion 984 or a back portion 986 of microcontroller device 900 and rotates the two portions towards each other about hinge 982 around utensil 920. Front portion 984 and back portion 986 may clip together with utensil 920 securely in between the two portions. Utensil channel 980 may include a non-slip material or texture in order to keep microcontroller device 900 from slipping off of utensil 920. With microcontroller device 900 securely attached to utensil 920, the user may use microcontroller device 900 similarly to other embodiments. Display 902 displays suggestions to the user while button 904 provides an input for the user. Logic 914 is programmed to suggest to the user, via display 902, a consuming action, or a suggestion to adjust the user's consumption of the meal. Sensor 906 determines whether or not utensil 920 is being used, and appropriately sends a signal to microcontroller 900.

Alternate embodiments make use of a vibrator as well to alert the user when the user attempts to perform a consuming action prior to the start of the next time interval.

The devices and methods disclosed above are merely exemplary embodiments of the present invention, but the present invention is not limited to functioning as a calorie pacer to slow eating habits. The user may be able to input desired settings and change the invention's operation to allow the user to increase their calories consumed as well, for instance to help people with eating disorders gain weight. This allows the present invention to be a fully functioning calorie control system and assist a user in reaching a variety of goals.

Furthermore, the present invention can be applied in many different ways related to the consumption of food. Liquid calories and consumption may be measured either by a straw-like device or measuring changes in weight. Calorie containing beverages and food can have their caloric density input by the user and the total calories consumed can be monitored and tabulated. Other embodiments incorporate the same designs and expand the device or system's ability to record data over the entire meal. An electronic table set may also be used in this fashion to record every action that occurs. The system of the present invention is used in a "smart place setting" that tracks everything from appetizers and drinks to desserts and coffees at the end of the meal.

Figure 10:
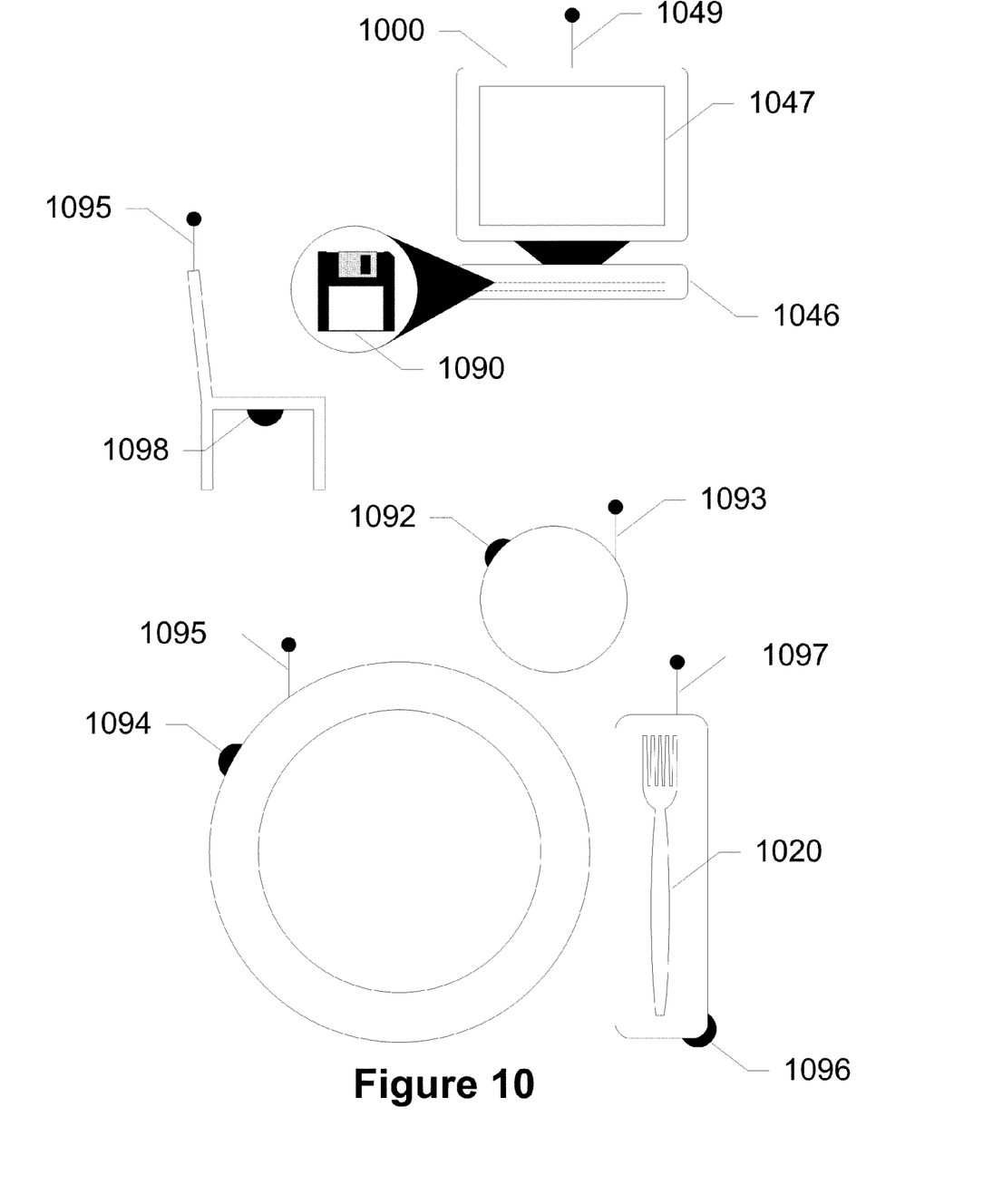
FIG. 10 discloses tableware incorporating a plurality of sensors, according to an exemplary embodiment of the present invention.

FIG. 10 shows tableware incorporating a plurality of sensors to create a smart place setting, according to an exemplary embodiment of the present invention. In this embodiment, the system includes a microcontroller 1000 in the form of a computer, a transceiver 1048 in communication with microcontroller 1000, a display 1044, a keyboard 1046, a logic 1090 onboard microcontroller 1000, a plate sensor 1094, a plate transceiver 1095, a glass sensor 1092, a glass transceiver 1093, a utensil sensor 1096, a utensil transceiver 1097, a chair sensor 1098, and a chair transceiver 1095. Plate sensor 1094, glass sensor 1092, and utensil sensor 1096 each contain weight sensors to determine the current weight of a meal, drink, etc. Transceiver 1048 communicates with plate transceiver 1095, glass transceiver 1093, and utensil transceiver 1097 to receive measurements, states, etc. from each of the sensors of the system. For instance, plate sensor 1094 may detect that two grams of food have been removed from the user's plate. Plate transceiver 1095 sends this measurement to transceiver 1048 of microcontroller 1000. Similarly, glass sensor 1092 may detect changes in the weight of the user's glass or may detect that the user has lifted his glass. These measurements or states are sent from glass transceiver 1093 to transceiver 1048 of microcontroller 1000. Chair sensor 1098 detects changes in the weight of the user. These measurements are sent from chair transceiver 1095 to transceiver 1048 of microcontroller 1000. Utensil sensor 1096 detects the presence or absence of a utensil 1020 as well as when utensil 1020 is replaced or removed, etc. Utensil transceiver 1097 transmits this information to transceiver 1048 of microcontroller 1000. Display 1044 displays suggestions to the user or users while keyboard 1046 provides an input for the user. Logic 1090 is programmed to suggest to the user, via display 1044, a consuming action, or a suggestion to adjust the user's consumption of the meal.

By using this "smart place setting", the system may be applied to more than just one individual. Whole families may be tracked and measured, allowing calorie control to be a group activity. The smart place setting can also be applied to any eatery or restaurant, allowing the establishment to track consumption statistics of their patrons or offer the system of the present invention as a "perk" to eating at that location. The system may also be implemented in hospitals, rehabilitation clinics, anywhere eating habits need adjustment.

Figure 11:
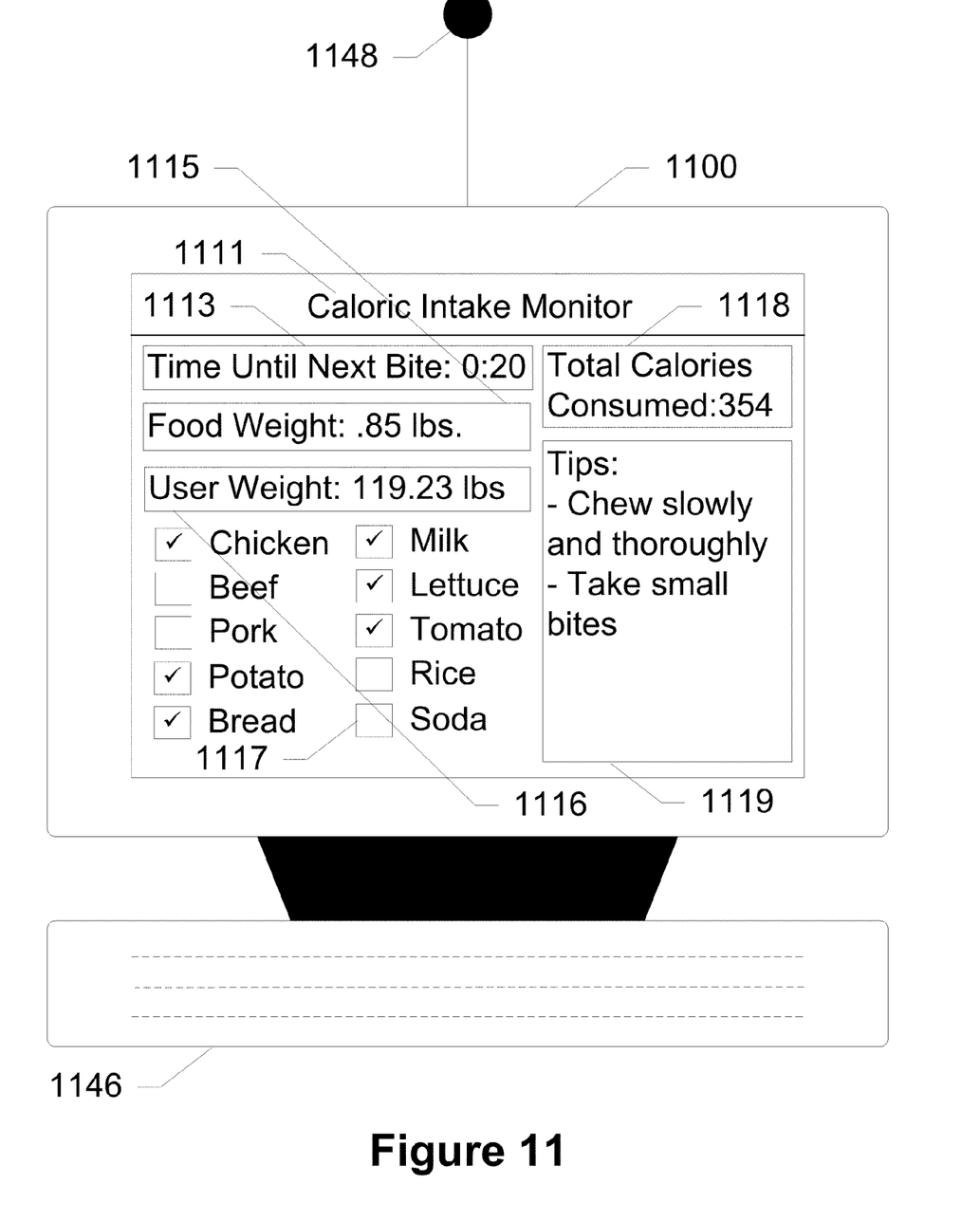
FIG. 11 shows a screenshot of a caloric intake monitor program, according to an exemplary embodiment of the present invention.

FIG. 11 shows a screenshot of a caloric intake monitor program 1111 on device 1100, according to an exemplary embodiment of the present invention. In this embodiment, caloric intake monitor program 1111 has a plurality of fields, including a time until next bite field 1113, a total calories consumed field 1118, a food weight field 1115, a user weight field 1116, a food selection field 1117, and a tips field 1119. Time until next bite field 1113 assists a user with caloric intake by notifying the user when to take another bite. Time until next bite field 1113 also notifies the user how long the user has to chew a current bite before the next bite. Total calories consumed field 1118 notifies the user of how many calories the user has consumed in the meal, in the day, in the week, etc., depending upon defined settings. Food weight field 1115 provides the weight of the portion of food being consumed and may be entered by the user or by sensors of the system. The weight of food provided in food weight field 1115 may decrease as the user consumes the portion of food. User weight field 1116 may be filled in by the user or by sensors of the system. Changes in this weight may be used to determine portions of food consumed by the user. This weight may also be used in determining portions, a rate of eating, etc. Food selection field 1117 allows the user to enter the type of food the user is eating. Food selection field 1117 may consist of check boxes with different types of food, a scroll menu, an entry, etc. Tips field 1119 provides the user with tips for the meal. These tips may include, for instance, "Chew slowly and thoroughly", or "Take small bites." An input, such as keyboard 1146, allows the user to change values of the fields, select fields, etc. An antenna 1148 connected to a transceiver of device 1100 allows device 1100 to communicate with sensors, other devices, etc.

In other exemplary embodiments of the caloric intake monitor program the food selection field gives more options. Many meals are a combination of food, and each item has a different amount of calories per pound. In addition to check boxes, the food selection field has weight entry for each item. In further embodiments the list includes many more items including, for instance, cuts of beef instead of a general beef checkbox, etc. In even further embodiments frozen meals, fast food items, etc. include a code to be entered which pulls the exact calorie count from a database. The database may be on the memory of the microcontroller or on a network in communication with the microcontroller such as a service provider network or the INTERNET.

Figure 12A:
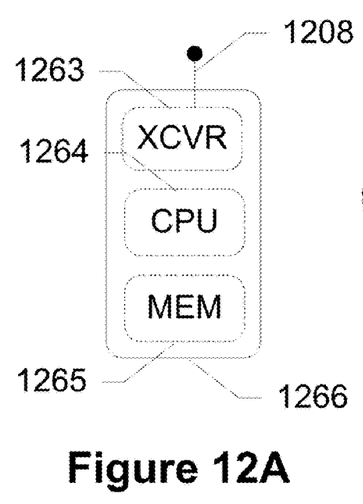
FIGS. 12A-12B show a tooth sensor according to an exemplary embodiment of the present invention.
Figure 12B:
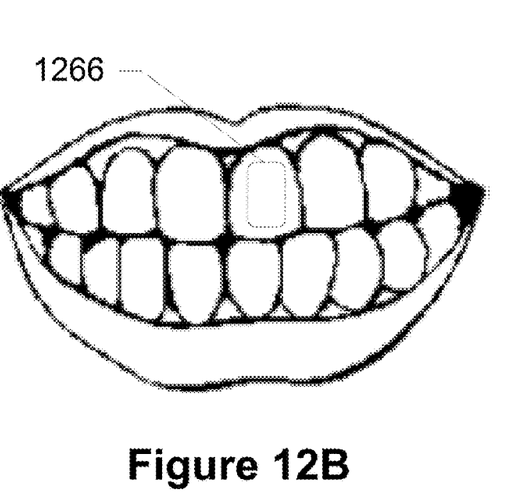

FIGS. 12A-12B show a tooth sensor 1266, according to an exemplary embodiment of the present invention. In this embodiment, tooth sensor 1266 includes an antenna 1208, a transceiver 1263, a central processing unit (CPU) 1264, and a memory 1265. Tooth sensor 1266 is affixed behind a tooth of a user using dental adhesives, etc. Alternatively, tooth sensor 1266 may be a part of a retainer, a cap on a tooth, etc. Tooth sensor 1266 is able to sense bites, chewing actions, etc. Thus, tooth sensor 1266 allows a system to determine the user's eating stage. CPU 1263 controls the other components of tooth sensor 1266 according to logic on memory 1265. Antenna 1208 with transceiver 1263 allows tooth sensor 1266 to communicate with the system.

Figure 13:
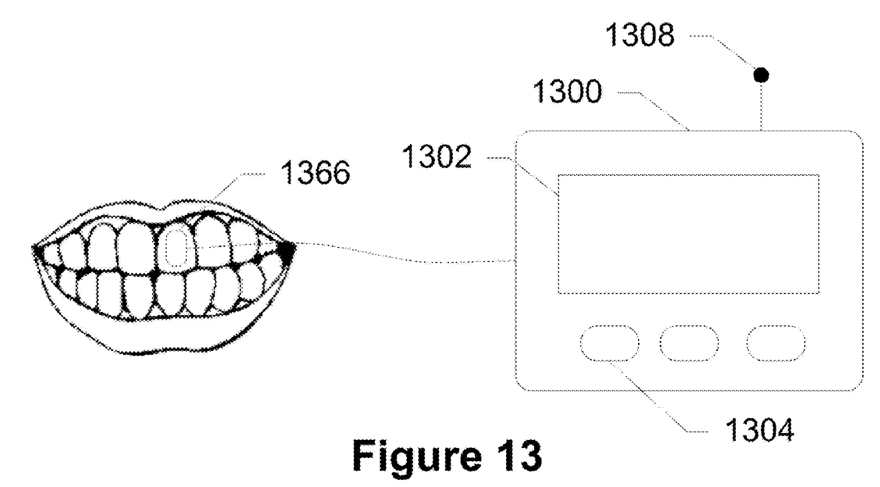
FIG. 13 shows a system for controlling caloric intake including a tooth sensor, according to an exemplary embodiment of the present invention.

FIG. 13 shows a system for controlling caloric intake including a tooth sensor 1366, according to an exemplary embodiment of the present invention. In this embodiment, tooth sensor 1366 is affixed to a tooth of a user. Tooth sensor 1366 wirelessly communicates with a microcontroller 1300. These communications include sensed number of bites, chewing motions, etc. Microcontroller 1300 receives these communications through antenna 1308 coupled to a transceiver. The user is able to view sensed information on a display 1302 of microcontroller 1300. An input button 1304 is available for the user to make selections, changes, etc. This method can monitor all food consumptions throughout the course of the day.

The foregoing disclosure of the exemplary embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A system for controlling caloric intake of a user, the system comprising:
    a microcontroller including a processor and a memory;
    an input in communication with the microcontroller;
    an output in communication with the microcontroller;
    a sensor in communication with the microcontroller; and
    a logic unit on the memory, the logic including
        detecting, via the sensor, a first consuming action performed by the user, and
        prompting the user to perform a second consuming action after a time interval.

2. The system of claim 1, wherein the input is one of a keyboard, a touchscreen, a scale sensor, and a microphone.

3. The system of claim 1, wherein the output is one of a display, a speaker, a plurality of light emitting diodes (LEDs), and a vibrator.

4. The system of claim 1, wherein the sensor is one of a presence sensor, a light sensor, a weight sensor, and an accelerometer.

5. The system of claim 1, further comprising a database stored on the memory, the database including a diet profile, the diet profile including one of a user profile associated with the user, and a meal profile.

6. The system of claim 5, wherein a user profile includes a plurality of statistics for the user, the statistics including a height, weight, and sex of the user.

7. The system of claim 1, wherein the sensor is coupled to a utensil.

8. The system of claim 1, wherein a plurality of sensors are coupled with a smart place setting.

9. The system of claim 1, further comprising a tooth sensor in communication with the microcontroller.

10. A device for controlling caloric intake of a user, the device comprising:
    a processor;
    a memory in communication with the processor;
    an input in communication with the processor;
    an output in communication with the processor;
    a sensor in communication with the processor; and
    a logic unit on the memory, the logic including
        detecting, via the sensor, a first consuming action performed by the user, and
        prompting the user to perform a second consuming action after a time interval.

11. The device of claim 10, wherein the sensor is one of a presence sensor, a light sensor, a weight sensor, and an accelerometer.

12. The device of claim 10, wherein the input is one of a keyboard, a touchscreen, and a microphone.

13. The device of claim 10, wherein the output is one of a display, a speaker, a plurality of light emitting diodes (LEDs), and a vibrator.

14. The device of claim 10, wherein the memory, processor, input, and output are enclosed within a housing that is adapted to be coupled to the utensil.

15. The device of claim 14, wherein the housing includes a clip removably attachable to an end of the utensil.

16. The device of claim 10, further comprising a transceiver in communication with a tooth sensor.

17. A method for monitoring and regulating a caloric intake of a user, the method comprising:

detecting a first consuming action performed by the user during a consumption of a meal; and prompting the user to perform a second consuming action after a time interval wherein the first consuming action is detected by a sensor and the second consuming action is prompted by an output.

18. The method of claim 17, further comprising:

detecting a time interval between the first consuming action and the second consuming action;

comparing the time interval with a stored time interval retrieved from a profile for the user; and prompting the user to adjust the time between a subsequent set of consuming actions.

19. The method of claim 17, further comprising:

defining a plurality of statistics for the user, the statistics including a height, weight, and sex of the user, and storing the plurality of statistics in a user profile.

20. The method of claim 19, further comprising:

recording a consumption pattern for the meal;

storing the consumption pattern in the user profile; and generating a consumption trend for the user over a specified number of meals.

21. The method of claim 20, further comprising:

defining a type of meal, storing the type of meal in a meal profile, and associating the meal profile with the user profile.

22. The method of claim 17, wherein the detecting comprises:

measuring a weight of a meal;

measuring an incremental decrease in the weight of the meal;

measuring an amount of calories using the weight of the meal consumed;

prompting the user to adjust a bite size and the time interval between consuming actions based in part upon the incremental decrease; and prompting the user to stop food consumption when satiation has been detected.

* * * * *